(12) United States Patent
Thakur et al.

(10) Patent No.: US 9,636,032 B2
(45) Date of Patent: May 2, 2017

(54) PERSISTENT DISPLAY OF NEAREST BEAT CHARACTERISTICS DURING REAL-TIME OR PLAY-BACK ELECTROPHYSIOLOGY DATA VISUALIZATION

(71) Applicant: Boston Scientific Scimed Inc., Maple Grove, MN (US)

(72) Inventors: Pramodsingh H. Thakur, White Bear Lake, MN (US); Shantha Arcot-Krishnamurthy, Vadnais Heights, MN (US); Allan C. Shuros, St. Paul, MN (US); Sunipa Saha, Shoreview, MN (US); Shibaji Shome, Arden Hills, MN (US); Barun Maskara, Blaine, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 14/270,867

(22) Filed: May 6, 2014

(65) Prior Publication Data

US 2014/0330150 A1    Nov. 6, 2014

Related U.S. Application Data

(60) Provisional application No. 61/820,142, filed on May 6, 2013.

(51) Int. Cl.
*A61B 5/044* (2006.01)
*A61B 5/042* (2006.01)
*A61B 5/00* (2006.01)

(52) U.S. Cl.
CPC ............ *A61B 5/044* (2013.01); *A61B 5/0422* (2013.01); *A61B 5/6858* (2013.01)

(58) Field of Classification Search
CPC ......... A61B 5/00; A61B 5/04; A61B 5/04011; A61B 5/044; A61B 5/6858
(Continued)

(56) References Cited

U.S. PATENT DOCUMENTS

| 4,649,924 A | 3/1987 | Taccardi |
| 4,674,518 A | 6/1987 | Salo |

(Continued)

FOREIGN PATENT DOCUMENTS

| CN | 1253761 A | 5/2000 |
| CN | 102917638 A | 2/2013 |

(Continued)

OTHER PUBLICATIONS

He, Ye H., "An interactive graphical system for automated mapping and display of cardiac rhythms", Journal of Electrocardiology, vol. 32, No. 3, Jul. 1, 1999, pp. 225-241.

(Continued)

*Primary Examiner* — Allen Porter, Jr.
(74) *Attorney, Agent, or Firm* — Faegre Baker Daniels LLP (57) ABSTRACT

A system and method for mapping an anatomical structure includes sensing activation signals of intrinsic physiological activity with a plurality of electrodes disposed in or near the anatomical structure. A most recent intrinsic event at a selected time is determined based on the sensed activation signals and a persistent display of relevant characteristics is generated based on the sensed activation signals of the most recent intrinsic event. The persistent display is updated upon detection of a subsequent intrinsic event.

11 Claims, 5 Drawing Sheets

(58) Field of Classification Search
USPC ............... 600/508, 509, 512, 515, 521, 523
See application file for complete search history.

(56) References Cited

U.S. PATENT DOCUMENTS

| | | |
|---|---|---|
| 4,840,182 A | 6/1989 | Carlson |
| 4,920,490 A | 4/1990 | Isaacson |
| 5,156,151 A | 10/1992 | Imran |
| 5,284,142 A | 2/1994 | Goble et al. |
| 5,297,549 A | 3/1994 | Beatty et al. |
| 5,300,068 A | 4/1994 | Rosar et al. |
| 5,341,807 A | 8/1994 | Nardella |
| 5,381,333 A | 1/1995 | Isaacson et al. |
| 5,469,858 A | 11/1995 | Osborne |
| 5,480,422 A | 1/1996 | Ben-Haim |
| 5,483,968 A | 1/1996 | Adam et al. |
| 5,500,011 A | 3/1996 | Desai |
| 5,553,611 A | 9/1996 | Budd et al. |
| 5,568,809 A | 10/1996 | Ben-Haim |
| 5,577,502 A | 11/1996 | Darrow et al. |
| 5,588,429 A | 12/1996 | Isaacson et al. |
| 5,634,469 A | 6/1997 | Bruder et al. |
| 5,647,870 A | 7/1997 | Kordis et al. |
| 5,662,108 A | 9/1997 | Budd et al. |
| 5,687,737 A | 11/1997 | Branham et al. |
| 5,697,377 A | 12/1997 | Wittkampf |
| 5,704,365 A | 1/1998 | Albrecht et al. |
| 5,722,402 A | 3/1998 | Swanson et al. |
| 5,840,025 A | 11/1998 | Ben-Haim |
| 5,840,031 A | 11/1998 | Crowley |
| 5,846,198 A | 12/1998 | Killmann |
| 5,848,972 A | 12/1998 | Triedman et al. |
| 5,876,336 A | 3/1999 | Swanson et al. |
| 5,921,982 A | 7/1999 | Lesh et al. |
| 5,954,665 A | 9/1999 | Ben-Haim |
| 5,971,933 A | 10/1999 | Gopakumaran et al. |
| 5,983,126 A | 11/1999 | Wittkampf |
| 6,014,581 A | 1/2000 | Whayne et al. |
| 6,050,267 A | 4/2000 | Nardella et al. |
| 6,070,094 A | 5/2000 | Swanson et al. |
| 6,095,150 A | 8/2000 | Panescu et al. |
| 6,167,296 A | 12/2000 | Shahidi |
| 6,226,542 B1 | 5/2001 | Reisfeld |
| 6,233,491 B1 | 5/2001 | Kordis et al. |
| 6,236,886 B1 | 5/2001 | Cherepenin et al. |
| 6,240,307 B1 | 5/2001 | Beatty et al. |
| 6,246,898 B1 | 6/2001 | Vesely et al. |
| 6,254,536 B1 | 7/2001 | DeVito |
| 6,278,894 B1 | 8/2001 | Salo et al. |
| 6,298,257 B1 | 10/2001 | Hall et al. |
| 6,308,093 B1 | 10/2001 | Armoundas et al. |
| 6,314,310 B1 | 11/2001 | Ben-Haim et al. |
| 6,317,619 B1 | 11/2001 | Boernert et al. |
| 6,318,375 B1 | 11/2001 | Plicchi et al. |
| 6,360,123 B1 | 3/2002 | Kimchi et al. |
| 6,368,285 B1 | 4/2002 | Osadchy et al. |
| 6,400,981 B1 | 6/2002 | Govari |
| 6,490,474 B1 | 12/2002 | Willis et al. |
| 6,516,807 B1 | 2/2003 | Panescu et al. |
| 6,547,082 B1 | 4/2003 | Babini |
| 6,556,695 B1 | 4/2003 | Packer et al. |
| 6,574,492 B1 | 6/2003 | Ben-Haim et al. |
| 6,574,498 B1 | 6/2003 | Gilboa |
| 6,593,884 B1 | 7/2003 | Gilboa et al. |
| 6,600,948 B2 | 7/2003 | Ben-Haim et al. |
| 6,603,996 B1 | 8/2003 | Beatty et al. |
| 6,631,290 B1 | 10/2003 | Guck et al. |
| 6,640,119 B1 | 10/2003 | Budd et al. |
| 6,650,927 B1 | 11/2003 | Keidar |
| 6,690,963 B2 | 2/2004 | Ben-Haim et al. |
| 6,701,176 B1 | 3/2004 | Halperin et al. |
| 6,728,562 B1 | 4/2004 | Budd et al. |
| 6,735,465 B2 | 5/2004 | Panescu |
| 6,773,402 B2 | 8/2004 | Govari et al. |
| 6,807,439 B2 | 10/2004 | Edwards et al. |
| 6,839,588 B1 | 1/2005 | Rudy |
| 6,847,839 B2 | 1/2005 | Ciaccio et al. |
| 6,872,428 B2 | 3/2005 | Yang et al. |
| 6,892,090 B2 | 5/2005 | Verard et al. |
| 6,892,091 B1 | 5/2005 | Ben-Haim et al. |
| 6,893,588 B2 | 5/2005 | Lawson et al. |
| 6,939,309 B1 | 9/2005 | Beatty et al. |
| 6,941,166 B2 | 9/2005 | MacAdam et al. |
| 6,957,101 B2 | 10/2005 | Porath et al. |
| 6,978,168 B2 | 12/2005 | Beatty et al. |
| 6,984,207 B1 | 1/2006 | Sullivan et al. |
| 6,990,370 B1 | 1/2006 | Beatty et al. |
| 7,016,719 B2 | 3/2006 | Rudy et al. |
| 7,043,292 B2 | 5/2006 | Tarjan et al. |
| 7,136,694 B2 * | 11/2006 | Hadley et al. ............... 600/515 |
| 7,263,397 B2 | 8/2007 | Hauck et al. |
| 7,505,810 B2 | 3/2009 | Harlev et al. |
| 7,515,954 B2 | 4/2009 | Harlev et al. |
| 7,629,981 B1 | 12/2009 | West |
| 7,729,752 B2 | 6/2010 | Harlev et al. |
| 8,103,338 B2 | 1/2012 | Harlev et al. |
| 8,137,343 B2 | 3/2012 | Harlev et al. |
| 8,463,368 B2 | 6/2013 | Harlev et al. |
| 8,498,699 B2 | 7/2013 | Wells et al. |
| 8,571,647 B2 | 10/2013 | Harlev et al. |
| 8,744,566 B2 | 6/2014 | Harlev et al. |
| 9,113,809 B2 | 8/2015 | Harlev et al. |
| 9,510,769 B2 | 12/2016 | Harlev et al. |
| 2002/0065459 A1 | 5/2002 | MacAdam et al. |
| 2002/0151807 A1 | 10/2002 | Goldin |
| 2003/0018251 A1 | 1/2003 | Solomon |
| 2003/0065271 A1 | 4/2003 | Khoury |
| 2003/0076277 A1 | 4/2003 | Muramatsu et al. |
| 2003/0078509 A1 | 4/2003 | Panescu |
| 2003/0093067 A1 | 5/2003 | Panescu |
| 2003/0216630 A1 | 11/2003 | Jersey-Willuhn et al. |
| 2004/0059237 A1 | 3/2004 | Narayan et al. |
| 2004/0077942 A1 | 4/2004 | Hall et al. |
| 2004/0097806 A1 | 5/2004 | Hunter et al. |
| 2004/0158165 A1 | 8/2004 | Yonce et al. |
| 2004/0243015 A1 | 12/2004 | Smith et al. |
| 2004/0254437 A1 | 12/2004 | Hauck et al. |
| 2005/0037489 A1 | 2/2005 | Gepstein et al. |
| 2005/0038337 A1 | 2/2005 | Edwards |
| 2005/0054918 A1 | 3/2005 | Sra |
| 2005/0107834 A1 | 5/2005 | Freeman et al. |
| 2005/0154282 A1 | 7/2005 | Li et al. |
| 2005/0288599 A1 | 12/2005 | MacAdam et al. |
| 2006/0085049 A1 | 4/2006 | Cory et al. |
| 2006/0116575 A1 | 6/2006 | Willis |
| 2006/0122526 A1 | 6/2006 | Berenfeld et al. |
| 2006/0173251 A1 | 8/2006 | Govari et al. |
| 2006/0178587 A1 | 8/2006 | Khoury |
| 2006/0241401 A1 | 10/2006 | Govari et al. |
| 2007/0016007 A1 | 1/2007 | Govari et al. |
| 2007/0038078 A1 | 2/2007 | Osadchy |
| 2007/0049821 A1 | 3/2007 | Willis |
| 2007/0112276 A1 * | 5/2007 | Simms, Jr. ............. A61B 5/046 600/515 |
| 2007/0197929 A1 | 8/2007 | Porath et al. |
| 2007/0232949 A1 | 10/2007 | Saksena |
| 2007/0255588 A1 | 11/2007 | Hamilton |
| 2007/0265539 A1 | 11/2007 | Hastings et al. |
| 2007/0270688 A1 | 11/2007 | Gelbart et al. |
| 2007/0270703 A1 | 11/2007 | He et al. |
| 2007/0287902 A1 | 12/2007 | Fuimaono et al. |
| 2007/0299351 A1 | 12/2007 | Harlev et al. |
| 2007/0299352 A1 | 12/2007 | Harlev et al. |
| 2007/0299353 A1 * | 12/2007 | Harlev et al. ............... 600/509 |
| 2008/0137934 A1 | 6/2008 | Sakaguchi et al. |
| 2008/0188765 A1 * | 8/2008 | Stolarski ............ A61B 5/04525 600/518 |
| 2008/0190438 A1 | 8/2008 | Harlev et al. |
| 2008/0221566 A1 | 9/2008 | Krishnan |
| 2008/0234588 A1 | 9/2008 | Feldman et al. |
| 2008/0249424 A1 | 10/2008 | Harlev et al. |
| 2008/0269813 A1 | 10/2008 | Greenhut et al. |
| 2009/0171274 A1 | 7/2009 | Harlev et al. |
| 2009/0177072 A1 | 7/2009 | Harlev et al. |

(56) References Cited

U.S. PATENT DOCUMENTS

| | | |
|---|---|---|
| 2009/0253976 A1 | 10/2009 | Harlev et al. |
| 2010/0268059 A1 | 10/2010 | Ryu et al. |
| 2010/0286551 A1 | 11/2010 | Harlev et al. |
| 2011/0206256 A1 | 8/2011 | Ramanathan et al. |
| 2011/0251505 A1 | 10/2011 | Narayan et al. |
| 2012/0029504 A1 | 2/2012 | Afonso et al. |
| 2012/0184858 A1 | 7/2012 | Harlev et al. |
| 2012/0184863 A1 | 7/2012 | Harlev et al. |
| 2012/0184865 A1* | 7/2012 | Harlev et al. ............... 600/509 |
| 2013/0035576 A1 | 2/2013 | O'Grady et al. |
| 2013/0079645 A1 | 3/2013 | Amirana et al. |
| 2013/0310702 A1 | 11/2013 | Daniel Martin Reinders et al. |
| 2014/0073194 A1 | 3/2014 | Lim et al. |
| 2014/0200874 A1 | 7/2014 | Zeng et al. |
| 2014/0235986 A1 | 8/2014 | Harlev et al. |
| 2014/0343388 A1 | 11/2014 | Thakur et al. |
| 2015/0254419 A1 | 9/2015 | Laughner et al. |
| 2015/0254893 A1 | 9/2015 | Laughner et al. |
| 2016/0051204 A1 | 2/2016 | Harlev et al. |

FOREIGN PATENT DOCUMENTS

| | | |
|---|---|---|
| EP | 2204120 A1 | 7/2010 |
| EP | 2427106 A | 3/2012 |
| EP | 2485194 A2 | 8/2012 |
| WO | 9905971 A1 | 2/1999 |
| WO | WO2006037172 A1 | 4/2006 |
| WO | 2007035306 A2 | 3/2007 |
| WO | 2007108776 A2 | 9/2007 |
| WO | 2007146364 A3 | 12/2007 |
| WO | 2010054320 A1 | 5/2010 |
| WO | 2010129095 A2 | 11/2010 |
| WO | WO2012037471 A2 | 3/2012 |
| WO | 2012092016 A1 | 7/2012 |
| WO | 2013006713 A2 | 1/2013 |
| WO | 2014185977 A1 | 11/2014 |
| WO | 2015134248 A1 | 9/2015 |

OTHER PUBLICATIONS

International Search Report and Written Opinion issued in PCT/US2014/036939, mailed Jul. 30, 2014, 11pages.
Buneo, Christopher A., Analyzing Neural Responses with Vector Fields, Journal of Neuroscience Methods, vol. 197, 2011, pp. 109-117.
He, Ye H. et al., "An Interactive Graphical System for Automated Mapping and Display of Cardiac Rhythms", Journal of Electrocardiology, vol. 32, No. 3, 1999, 17 pages.
Holm, Magnus et al. A New Method for Analysis of Atrial Activation During Chronic Atrial Fibrillation in Man. IEEE Transactions on Biomedical Engineering, 43(2): 193-210, Feb. 1996.
International Search Report arid Written Opinion issued in PCT/US2014/000114, mailed Sep. 8, 2014, 12 pages.
Gitosusastro et al., Performance Derivative Calculations arid Optimization Process, IEEE Transactions on Magnetics, vol. 25, No. 4 (Jul. 1989) pp. 2834-2839.
International Preliminary Report on Patentability issued in PCT/US2014/000114, mailed Nov. 26, 2015, 9 pages.
International Preliminary Report on Patentability issued in PCT/US2014/036939, mailed Nov. 19, 2015, 8 pages.
International Search Report and Written Opinion issued in PCT/US2015/017289, mailed May 6, 2015, 10 pages.
International Search Report and Written Opinion issued in PCT/US2015/017482, mailed Jun. 5, 2015, 9 pages.
Laciar et al., Improved Alignment Method for Noisy High-Resolution ECG and Holter Records Using a Muitiscale Cross-Correlation, IEEE Transactions on Biomedical Engineering, 50(3), pp. 344-353, 2003
Liu et al., "Endocardial Potential Mapping from a Noncontact Nonexpandable Catheter: A Feasibility Study", Annals of Biomedical Engineerina, 26:994-1009, 1998.
Lorensen et al. "Marching Cubes: a High Resolution 3D Surface Construction Algorithm", Computer Graphics, 21 (4):163-169, Jul. 1987.
Makela et al., "A Review of Cardiac Image Registration Methods", IEEE Transactions on Medical Imaging, 21 (9):1011-1021, Sep. 2002.
Malladi R. "Geometric Approach to Segmentation and Analyis of 3D Medical Images" Mathematical Methods in Biomedical Image Analysis, Proceedings of the Workshop on, Jun. 21-22, 1996, pp. 244-252.
Mangan, Alan et al., "Partitioning 3D Surface Meshes Using Watershed Segmentation", IEEE Transactions on Visualization and Computer Graphics, vol. 05, No. 4, pp. 308-321, (Oct.-Dec. 1999).
Meininger et al., "Initial Experience with a Novel Focused Ultrasound Ablation System for Ring Ablation Outside the Pulmonary Vein", Journal of Interventional Cardiac Electrophysiology, 8:141-148, 2003.
Merrill, Daniel R. et al., "Electrical stimulation of excitable tissue: design of a efficacious and safe protocols", Journal of Neuroscience Methods, vol. 141, pp. 171-198 (2005).
Miller, "Editor's Forum—Application of Registration for Ablation: A Marriage of Technologies", Journal of Interventional Cardiac Electrophysiology, 11:87-89, 2004.
Nademanee et al., "A New Approach for Catheter Ablation of Atrial Fibrillation: Mapping of the Electrophysiologic Substrate", Journal of the American College of Cardiology, 43(11):2044-2053, 2004.
Non-final Office Action issued in U.S. Appl. No. 11/451,898, mailed Sep. 25, 2008, 13 pages.
Non-final Office Action issued in U.S. Appl. No. 11/451,908, mailed Sep. 4, 2008, 12 pages.
Noseworthy et al., "The Impact of Respiration on Left Atrial and Pulmonary Venous Anatomy: Implications for Image-Guided Intervention", Heart Rhythm, 2(11), pp. 1173-1178, Nov. 2005.
Pappone et al., "Robotic Magnetic Navigation for Atiral Fibrillation Ablation" Journal of the American College of Cardiology, 47(7):1390-1400, 2006.
Paragios "A Level Set Approach for Shape-Driven Segmentation and Tracking of the Left Ventricle"IEEE Transactions on Medical Imaging, 22(6):773-776, Jun. 2003.
Persson et al., "A Simple Mesh Generator in MATLAB", Siam Review, 46(2):329-345, 2004.
Persson, "Mesh Generation for implicit Geornetrics", Massachusetts Institute of Technology—Thesis, Feb. 2005.
Pham, Dzung et al., "Current Methods in Medical image Segmentation", Annu. Rev. Biomed. Eng., 02: pp. 315-337, (2000).
Rao et al., "Novel Noncontact Catheter System for Endocardial Electrical and Anatomical Imaging", Annals of Biomedical Engineering, 32(4):573-584, 2004.
Reddy et al., "Integration of Cardiac Magnetic Resonance Imaging With Three-Dimensional Electroanatomic Mapping to Guide Left Ventricular Catheter Manipulation—Feasibility in a Porcine Model of Healed Myocardial Infarction", Journal of the American College of Cardiology, 44(11):2202-2213, 2004.
Reddy et al., "Use of a Diode Laser Balloon Ablation Catheter to Generate Circumferential Pulmonary Venous Lesions in an Open-Thoracotomy Caprine Model", PACE, 27:52-57, 2004.
Sanders et al., "Spectral Analysis Identifies Sites of High-Frequency Activity Maintaining Atrial Fibrillation in Humans", Circulation, 112:789-797, 2005.
Sethian, "Level Set Methods and Fast Marching Methods: Evolving Interlaces in Computational Geometry, Fluid Mechanics, Computer Vision, and Materials Science", Department of Mathematics-University of California, Berkeley, Cambridge University Press, 1999.
Simon et al., "Electroanatomic Mapping of the Right Atrium With a Right Atrial Basket Catheter and Three-Dimensional Intracardiac Echocardiography", PACE, 27:318-326, 2004.
Smits et al., "Catheter-Based Intramyocardial Inection of Autologous Skeletal Myoblasts as a Primary Treatment of Ischemic Heart Failure", Journal of the American College of Cardiology, 42(12):2063-2069, 2003.
Solomon et al., "Real-Time Cardiac Catheter Navigation on Three-Dimensional CT Images", Journal of Interventional Cardiac Electrophysiology, 8:27-36, 2003.

(56) References Cited

OTHER PUBLICATIONS

Sra et al., "Registration of Three-Dimensional Left Atrial Computed Tomographic Images With Projection Images Obtained Using Fluoroscopy", Circulation, 112:3763-3768, 2005.
Sra, Jasbir et al, "Registration Of 3D Computed Tomographic Images With Interventional Systems: Implications For Catheter Ablation Of Atrial Fibrillation", J Interv Card Electrophysiol, 16:141-148, 2006.
Stevenson, "Radiofrequency Catheter Ablation of Ventricular Tachycardia After Myocardial Infarction", Circulation, 98:308-314, 1998.
Supplemental European Search Report issued in EP App[iication 10772414.8, mailed May 7, 2013, 6 pages.
Supplemental European Search Report issued in EP Application No. 09824015, mailed Jun. 1, 2012, 7 pages.
Supplementary European Search Report issued in EP Applicaion No. 09727423, mailed May 15, 2012, 5 pages.
Supplementary European Search Report issued in EP Application No. 07798369.0 mailed Jul. 30, 2010, 6 pages.
Supplementary Europeant Search Report issued in EP Application No. 08728501, mailed Feb. 25, 2011, 4 pages.
Taccardi et al., "A New Intracavitary Probe for Detecting the Site of the Origin of Ectopic Ventricular Beats During One Cardiac Cycle", Circulation, 75(1):272-281, 1987.
Thal et al., "Novel Applications in Catheter Ablation", Journal of Interventional Cardiac Electrophysiology, 13:17-21, 2005.
Thiagalingarn et al., "Noncontact Mapping of the Left Ventricle: Insights from Validation With Transmural Contact Mapping", PACE, 27:570-578, 2004.
Voth, "The Inverse Problem of Electrocardiography: Industrial Solutions and Simulations", BEM and NFSI Conference Proceedings, Minneapolis, MN, May 12-15, 2005, pp. 191-194.
Wittkarripf et al., "LocaLisa: New Technique for Real-Time 3-Dimensional Localization of Regular Intracardiac Electrodes", Circulation, 99:1312-1317, 1999.
Yezzi, Anthony et al,, "A Geometric Snake Model for Segmentation of Medical Imagery", IEEE Transactions on Medical Imag, vol. 16, No. 2, Apr. 1997.
Adams et al., "Seeded Region Growing", IEEE Transactions on Pattern Analysis and Machine Intelligence, 16(6):641-647, 1994.
Arthur et al., "Clinical Use of Intracardiac Impedance: Current Applications and Future Perspectives", PACE, vol. 24, No. 4, Part 1, Apr. 2001 pp. 500-506.
Baan, Jan et al., "Continuous Measurement of Left Ventricular Volume in Animals And Humans by Conductance Catheter", Diagnostic Methods-Conductance Catheter, Circulation, vol. 70, No. 5, 1984, pp. 812-823.
Badics et al., "Real-Time Reconstruction of Endocardial Potential Maps in Non-Contact Cardiac Mapping", International Journal for computation and Mathematics in Electrical and Electronic Engineering (COMPEL), vol. 28, No. 4, 2009
Ben-Haim et al., "Nonfluoroscopic, in Vivo Navigation and Mapping Technology", Nature Medicine 2(12):1393-1395, Dec. 1996.
Besl et al., "A Method for Registration of 3-D hapes", IEEE Transactions on Pattern Analysis and Machine Intelligence, 14(2):239-256, Feb. 1992.
Blomstrom-Lundqvist et al., "ACC/AHA/ESC Guidelines for the Management of Patients With Supraventricular Arrhythmias-Executive Summary", Journal of the American College of Cardiology, 42(8):1493-1531, 2003.
Breithardt et al., "AHA Medical/Scientific Statement—Special Report: Standards for Analysis of Ventricular Late Potentials Using High-Resolution or Signal-Averaged Electrocardiography", Circuiation, 83(4):1481-1488, Apr. 1991.
Brooks et al., "Electrical Imaging of the Heart", IEEE Signal Processing Magazine, pp. 24-42, 1997.
Caspi et al., "Stem Cell Research: Regenerating the Heart Using Human Embryonic Stem Cells—from Cell to Bedside", IMAJ 8:208-214, 2006.

Cheney et al., "Electrical Impedance Tomography", SIAM Review 41(1):85-101, 1999.
Communication pursuant to Article 94(3) EPC issued in EP Application No. 07 798 369.0, mailed Nov. 17, 2011, 5 pages.
De Groot et al., "Three-Dimensional Catheter Positioning During Radiofrequency Ablation in Patients: First Application of a Real-Time Position Management System", Journal of Cardiovascular Electrophysiology, 11(11):1183-1192, Nov. 2000.
Donahue et al., "Focal Modification of Electrical Conduction in the Heart by Viral Gene Transfer", Nature Medicine, 6 (12):1395-1398, 2000.
Dong et al., "Integrated Electroanatomic Mapping With Three-Dimensional Computed Tomographic Images for Real-Time Guided Ablations", Circulation 113:186-194, 2006.
Durrer et al., "Total Excitation of the isolated Human Heart", Circulation, vol. XLI, pp. 899-912, 1970.
E. J. Haug et al.: Design Sensitivity Analysis of Structural Systems, Mathematics in Science and Engineering, vol. 177 (1986).
Ector et al., "Cardiac Three-Dimensional Magnetic Resonance Imaging and Fluoroscopy Merging—A New Approach for Electroanatomic Mapping to Assist Catheter Ablation", Circulation, (Dec. 13, 2005), pp. 3769-3776
Extended European Search Report issued in EP Application No. 10 772 414, maiied May 7, 2013, 6 pages.
Fletcher, R. "Chapter 6: Sums of Squares and Nonlinear Equations," Practical Methods of Optimization, 2nd Edition, J. Willey & Sons, pp. 110-119 (1987).
Friedman, "Catheter Cryoablation of Cardiac Arrhythrnias", Current Opinion in Cardiology, 20:48-54, 2005.
Friedman, "Novel Mapping Techniques for Cardiac Electrophysiology", Heart 2002, 87:575-582.
Geddes, L.A. et al., "Criteria for the Selection of Materials for Implanted Electrodes", Annals of Biomedical Engineering, vol. 31, pp, 879-890 (2003).
Gepstein et al., "A Novel Method for Nonfluoroscopic Catheter-Based Electroanatomical Mapping of the Heart", Circulation 95:1611-1622, 1997.
Hansen: Rank-Deficient arid Discrete III-Posed Problems: Numerical Aspects of Linear Inversion, SIAM, Philadelphia, USA, pp. 100-103, 1998.
Huang, Yi-Chih et al., "Development of a Third Generation Intraventricular Impedance Imaging (III) System: Evaluation of Hardware Design", Engineering in Medicine and Biology Society,. Proceedings of the 19th Annual International Conference of the IEEE, Oct. 30-Nov. 2, 1997 vol. 6, pp. 336-338 (1997).
International Preliminary Report on Patentability in PCT/US2007/070854, Issued on Dec. 16, 2008, 9 pages.
International Preliminary Report on Patentability in PCT/US2009/061277, issued May 3, 2011 11 pages.
International Preliminary Report on Patentability in PCT/US2010/027568 issued on Oct. 25, 2011, 4 pages.
International Preliminary Report on Patentability issued in PCT/US2008/052385 on Aug. 11, 2009, 6 pages.
International Preliminary Report on Patentability issued in PCT/US2009/036099, mailed Oct. 14, 2010, 20 pages.
International Preliminary Report on Patentability issued in PCT/US2010/027436, issued Nov. 9, 2011, 4 pages.
International Preliminary Report on Patentability issued in PCT/US2015/0017289 mailed Sep. 15, 2016, 8 pages.
International Search Report and the Written Opinion in PCT/US08/52385 mailed Aug. 8, 2008, 11 pages.
International Search Report and Written Opinion in PCT/US2010/027568, mailed Nov. 4, 2010, 6 pages.
International Search Report andWritten Opinion in PCT/US2012/020946, mailed May 7, 2012, 15 pages.
International Search Report and Written Opinion issued in PCT/US2007/070854, mailed Sep. 12, 2008, 10 pages.
International Search Report and Written Opinion issued in PCT/US2009/036099, mailed Apr. 28, 2009, 21 pages.
International Search Report and Written Opinion issued in PCT/US2009/061277, mailed Apr. 8, 2010, 12 pages.
International Search Report and Written Opinion issued in PCT/US2010/027436 mailed Oct. 27, 2010, 10 pages.

(56) References Cited

OTHER PUBLICATIONS

Jain et al., "Cell Therapy Attenuates Deleterious Ventricular Remodeling and Improves Cardiac Performance after Myocardial Infarction", Circulation, 103:1920-1927, 2001.

Jaffe, "Rotors and Spiral Waves in Atrial Fibrillation", Journal of Cardiovascular Electrophysiology, 14:776-780, 2003.

Jane et al., "Alignment Methods .For Averaging of High-Resolution Cardiac Signals: A Comparative Study of Performance", IEEE Transactions on Biomedical Engineering, 38(6):571-579, 1991.

Japanese Office Action in JP Application No. 2009-515586, dated Jun. 26, 2012, 4 pages (0002JP1).

Jia et al., "Electrophysiologic Endocardial Mapping from a Noncontact Nonexpandable Catheter: A Validation Study of a Geometry-Based Concept". Journal of Cardiovascular Electrophysiology, 11:1238-1251, 2000.

Kikuchi et al,, "Targeted Modification of Atria: Electrophysiology by Homogeneous Transmurai Atria: Gene Transfer", Circulation, 111:264-270, 2005.

Kistler et al., "Validation of Three-Dimensional Cardiac Image integration: Use of Integrated CT lmage into Electroanatomic Mapping System to Performa Catheter Ablation of Atrial Fibrillation", Journal of Cardiovascular Electrophysiology, 17:341-348, 2006.

Kukiik et al., "The reconstruction, from a set of points, arid anaiysis of the interior surface of the heart chamber", Physiol. Meas. 25:617-627, 2004.

Kun, Stevan et al., "Conductance Volumetric Model of an Eccentrically Positioned Catheter Within a Three-Compartment Ellipsoidal Ventricle", IEEE Transactions on Biomedical Engineering, vol. 40, No. 6, Jun. 1993, pp. 589-592.

L. Piegi, W. Tiller: The NURBS Book, 2nd Edition, Monographs in Visual Communication, Springer (1997).

International Search Report on Patentability issued in PCT/US2015/017482 mailed Sep. 15, 2016, 4 pages.

Andras Lasso et al., "SlicerWiki VolumeClip", Dec. 25, 2014, pp. 1-4, XP55332376, retrieved from teh internet: https://www.slicer.org/wiki/Documentation/4.4/Extensions/VolumeClip, retrieved on Jan. 5, 2017.

Anonymous: Solid Commands—Rhino 3-D Modeling (Rhinoceros 5), Sep. 17, 2015, XP055332631, Retrieved from Internet: http://docs.mcneel.com/rhino/5/help/en-us/seealso/sak_solidtools.htm, retrieved on Jan. 5, 2017, see under Cap, 2 pages.

International Search Report and Written Opinion issued in PCT/US2016/053630, mailed Jan. 17, 2017, 12 pages.

International Search Report and Written Opinion issued in PCT/US2016/053633, mailed on Jan. 17, 2017, 14 pages.

\* cited by examiner

PERSISTENT DISPLAY OF NEAREST BEAT CHARACTERISTICS DURING REAL-TIME OR PLAY-BACK ELECTROPHYSIOLOGY DATA VISUALIZATION

CROSS-REFERENCE TO RELATED APPLICATION

This application claims priority to Provisional Application No. 61/820,142, filed May 6, 2013, which is herein incorporated by reference in its entirety.

TECHNICAL FIELD

The present disclosure relates to cardiac mapping systems. More specifically, the present disclosure relates to a cardiac mapping system configured to display persistent data visualization during an electrophysiological study.

BACKGROUND

Diagnosing and treating heart rhythm disorders often involve the introduction of a catheter having a plurality of sensors/probes into a cardiac chamber through the surrounding vasculature. The sensors detect electric activity of the heart at sensor locations in the heart. The electric activity is generally processed into electrogram signals that represent signal propagation through cardiac tissue at the sensor locations.

Systems can be configured to display the electrical signals detected in the cardiac chamber in a real-time fashion to a physician. However, the activation signals are transient and thus are replaced by a display of the most current electrical activity including uninteresting activity, for example the dormant electrical signals between heart beats. While a visualization of the temporal evolution of these electrical signals can be useful in diagnosing cardiac abnormalities, it may be beneficial to display various characteristics of the electrical signals in a persistent fashion or until a significant change in the electrical signals is detected.

SUMMARY

Disclosed herein are various embodiments of a method for generating a persistent display of cardiac activation signals sensed by a cardiac catheter, as well as anatomical mapping systems employing such methods.

In Example 1, a method for mapping an anatomical structure includes sensing activation signals of intrinsic events with a plurality of electrodes disposed in or near the anatomical structure, determining a most recent intrinsic event at a first time based on the sensed activation signals, generating a persistent display of at least one relevant characteristic of the sensed activation signals of the most recent intrinsic event, and updating the persistent display upon detection of a subsequent intrinsic event.

In Example 2, the method according to Example 1, wherein the persistent display is generated in real-time as the activation signals are sensed.

In Example 3, the method according to either Examples 1 or 2, wherein the persistent display is generated off line after a plurality of activation signals are recorded and the most recent intrinsic event is before or after the first time.

In Example 4, the method according to any of Examples 1-3, wherein the generated persistent display includes at least one of an activation map, a vector field representing an activation pattern during the most recent intrinsic event, a contour map of iso-potential lines during the most recent intrinsic event, and a reliability map of related to onset pick-up times of the activation signals of the most recent intrinsic event.

In Example 5, the method according to any of Examples 1-4, further includes determining an onset time for the most recent activation signal at each of the plurality of electrodes, calculating a median onset time based on an average of the determined onset times, and identifying the subsequent intrinsic event according to the calculated median onset time.

In Example 6, the method according to any of Examples 1-5, further includes calculating a quadratic mean for the most recent activation signal for each of the plurality of electrodes, determining a peak value from a sum of the quadratic means, and identifying the subsequent intrinsic event according to the determined peak value.

In Example 7, the method according to any of Examples 1-6, further includes determining an onset time for the most recent activation signal at each of the plurality of electrodes, convolving the onset times with a Gaussian function, identifying the subsequent intrinsic event according to the convolution.

In Example 8, the method according to any of Examples 1-7, further includes determining a morphology for each intrinsic event, comparing the morphology of the most recent intrinsic event with a previous intrinsic event, and updating the persistent display based on changes in morphology between the most recent and previous intrinsic event.

In Example 9, the method according to any of Examples 1-8, wherein the persistent display is updated upon the detection of a plurality of subsequent intrinsic events.

In Example 10, a method for cardiac mapping includes sensing activation signals of cardiac activity with a plurality of electrodes disposed in or near in myocardial tissue, detecting a most recent heart beat based on the sensed activation signals generating a persistent display of at least one relevant characteristic associated with the sensed activation signals of the most recent heart beat, and updating the persistent display upon detection of a subsequent heart beat.

In Example 11, the method according to Example 10, wherein the generated persistent display includes at least one of an activation map during the most recent heart beat, a vector field representing an activation pattern during the most recent heart beat, a contour map of iso-potential lines during the most recent heart beat, and a reliability map of related to onset pick-up times of the activation signals related to the most recent heart beat.

In Example 12, the method according to either Examples 10 or 11, further included determining an onset time for a most recent activation signal at each of the plurality of electrodes, calculating a median onset time based on an average of the determined onset times, and detecting the subsequent heart beat based on the calculated median onset time.

In Example 13, the method according to any of Examples 10-12, further includes calculating a quadratic mean for a most recent activation signal for each of the plurality of electrodes, determining a peak value from a sum of the quadratic means, and detecting the subsequent heart beat based on the determined peak value.

In Example 14, the method according to any of Examples 10-13, further includes determining an onset time for a most recent activation signal for each of the plurality of electrodes, convolving the onset times with a Gaussian function, and detecting the subsequent heart beat according to the convolution.

In Example 15, the method according to any of Examples 10-14, further includes determining a morphology for each heart, comparing the morphology of the most recent heart beat with a previous heart beat, and updating the persistent display based on changes in morphology between the most recent and previous heart beat.

In Example 16, an anatomical mapping system includes a plurality of mapping electrodes configured to detect activation signals of intrinsic events within an anatomical structure, each of the plurality of mapping electrodes having an electrode location, and a processing system associated with the plurality of mapping electrodes, the processing system configured to record the detected activation signals and associate at least one of the plurality of mapping electrodes with each recorded activation signal, the processing system further configured to determine a most recent intrinsic event, to generate a persistent display of at least one relevant characteristic of the detected activation signals of the most recent intrinsic event, and to update the persistent display with at least one relevant characteristic of a subsequent intrinsic event.

In Example 17, the anatomical system according to Example 16, wherein the persistent display includes at least one of a vector field representing an activation pattern during the most recent intrinsic event, a contour map of iso-potential lines during the most recent intrinsic event, and a reliability map of onset pick-up times of the most recent intrinsic event.

In Example 18, the anatomical system according to either of Examples 16 or 17, wherein, to determine the most recent intrinsic event, the processing system is further configured to determine an onset time for the most recent activation signal at each of the plurality of electrodes, and to calculate a median onset time based on an average of the determined onset times.

In Example 19, the anatomical system according to any of Examples 16-18, wherein, to determine the most recent intrinsic event, the processing system is further configured to calculate a quadratic mean for the most recent activation signal for each of the plurality of electrodes, and to determine a peak value from a sum of the quadratic means.

In Example 20, the anatomical system according to any of Examples 16-19, wherein, to determine the most recent intrinsic event, the processing system is further configured to determine an onset time for the most recent activation signal at each of the plurality of electrodes, and to convolve the onset times with a Gaussian function.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
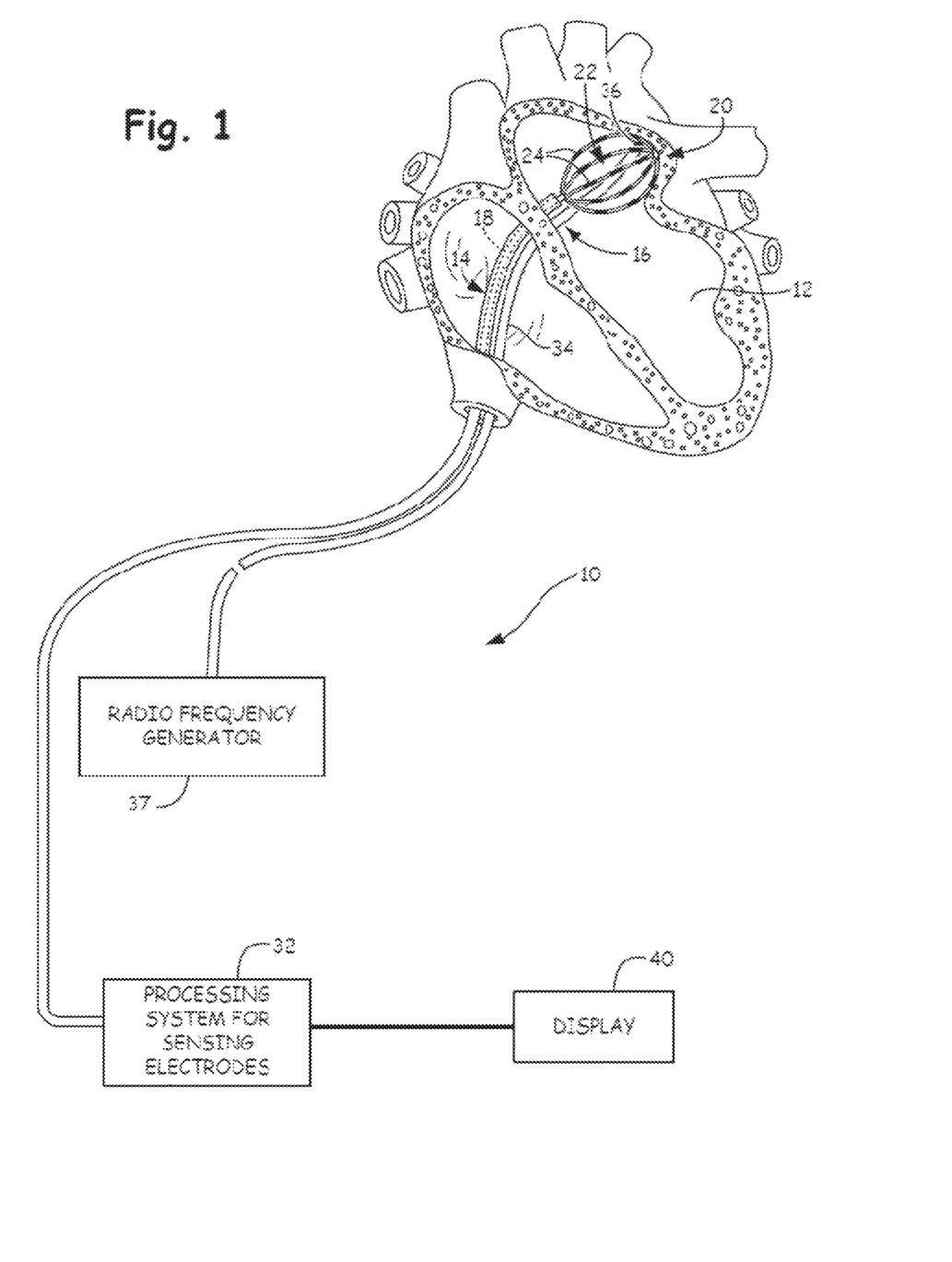
FIG. 1 is a schematic view of an embodiment of a system for accessing a targeted tissue region in the body for diagnostic and therapeutic purposes.

FIG. 1 is a schematic view of a system 10 for accessing a targeted tissue region in the body for diagnostic or therapeutic purposes. FIG. 1 generally shows the system 10 deployed in the left ventricle of the heart. Alternatively, system 10 can be deployed in other regions of the heart, such as the left atrium, right atrium, or right ventricle. While the illustrated embodiment shows the system 10 being used for ablating myocardial tissue, the system 10 (and the methods described herein) may alternatively be configured for use in other tissue ablation applications, such as procedures for ablating tissue in the prostrate, brain, gall bladder, uterus, and other regions of the body, including in systems that are not necessarily catheter-based.

The system 10 includes a mapping probe 14 and an ablation probe 16. In FIG. 1, each is separately introduced into the selected heart region 12 through a vein or artery (e.g., the femoral vein or artery) through suitable percutaneous access. Alternatively, the mapping probe 14 and ablation probe 16 can be assembled in an integrated structure for simultaneous introduction and deployment in the heart region 12.

The mapping probe 14 has a flexible catheter body 18. The distal end of the catheter body 18 carries a three-dimensional multiple electrode structure 20. In the illustrated embodiment, the structure 20 takes the form of a basket defining an open interior space 22 (see FIG. 2), although other multiple electrode structures could be used wherein the geometry of the electrode structure and electrode locations are known. The multiple electrode structure 20 carries a plurality of mapping electrodes 24 each having an electrode location and channel. Each electrode 24 is configured to sense intrinsic physiological activity in the anatomical region on which the ablation procedure is to be performed. In some embodiments, the electrodes 24 are configured to detect activation signals of the intrinsic physiological activity within the anatomical structure, e.g., the activation times of cardiac activity.

The electrodes 24 are electrically coupled to a processing system 32. A signal wire (not shown) is electrically coupled to each electrode 24 on the basket structure 20. The wires extend through the body 18 of the probe 14 and electrically couple each electrode 24 to an input of the processing system 32, as will be described later in greater detail. The electrodes 24 sense intrinsic electrical activity in the anatomical region, e.g., myocardial tissue. The sensed activity, e.g. activation signals, is processed by the processing system 32 to assist the physician by generating an anatomical map, e.g., action potential duration (APD) map or an activation map, to identify the site or sites within the heart appropriate for ablation. The processing system 32 identifies a near-field signal component, i.e. activation signals associated with local activation and originating from the tissue adjacent to the mapping electrode 24, from an obstructive far-field signal component, i.e. activation signals originating from non-adjacent tissue, within the sensed activation signals. For example, in an atrial study, the near-field signal component includes activation signals originating from atrial myocardial tissue whereas the far-field signal component includes activation signals originating from the ventricular myocardial tissue. The near-field activation signal component can be further analyzed to find the presence of a pathology and to determine a location suitable for ablation for treatment of the pathology, e.g., ablation therapy.

The processing system 32 includes dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired activation signals. In some embodiments, the processing system 32 includes a general purpose microprocessor and/or a specialized microprocessor (e.g., a digital signal processor, or DSP, which may be optimized for processing activation signals) that executes instructions to receive, analyze and display information associated with the received activation signals. In such implementations, the processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that the processing system 32 can take any suitable form.

In some embodiments, the processing system 32 may be configured to measure the intrinsic electrical activity in the myocardial tissue adjacent to the electrodes 24. For example, in some embodiments, the processing system 32 is configured to detect intrinsic electrical activity associated with a dominant rotor in the anatomical feature being mapped. Studies have shown that dominant rotors have a role in the initiation and maintenance of atrial fibrillation, and ablation of the rotor path and/or rotor core may be effective in terminating the atrial fibrillation. In either situation, the processing system 32 processes the sensed activation signals to isolate the near-field signal component and generate an APD map based on the isolated near-field signal component. The APD map may be used by the physician to identify a site suitable for ablation therapy.

The ablation probe 16 includes a flexible catheter body 34 that carries one or more ablation electrodes 36. The one or more ablation electrodes 36 are electrically connected to a radio frequency (RF) generator 37 that is configured to deliver ablation energy to the one or more ablation electrodes 36. The ablation probe 16 is movable with respect to the anatomical feature to be treated, as well as the structure 20. The ablation probe 16 is positionable between or adjacent to electrodes 24 of the structure 20 as the one or more ablation electrodes 36 are positioned with respect to the tissue to be treated.

The processing system 32 outputs to a device 40 the generated APD map for viewing by a physician. In the illustrated embodiment, device 40 is a CRT, LED, or other type of display, or a printer. The device 40 presents the APD map in a format most useful to the physician. In addition, the processing system 32 may generate position-identifying output for display on the device 40 that aids the physician in guiding the ablation electrode(s) 36 into contact with tissue at the site identified for ablation.

Figure 2:
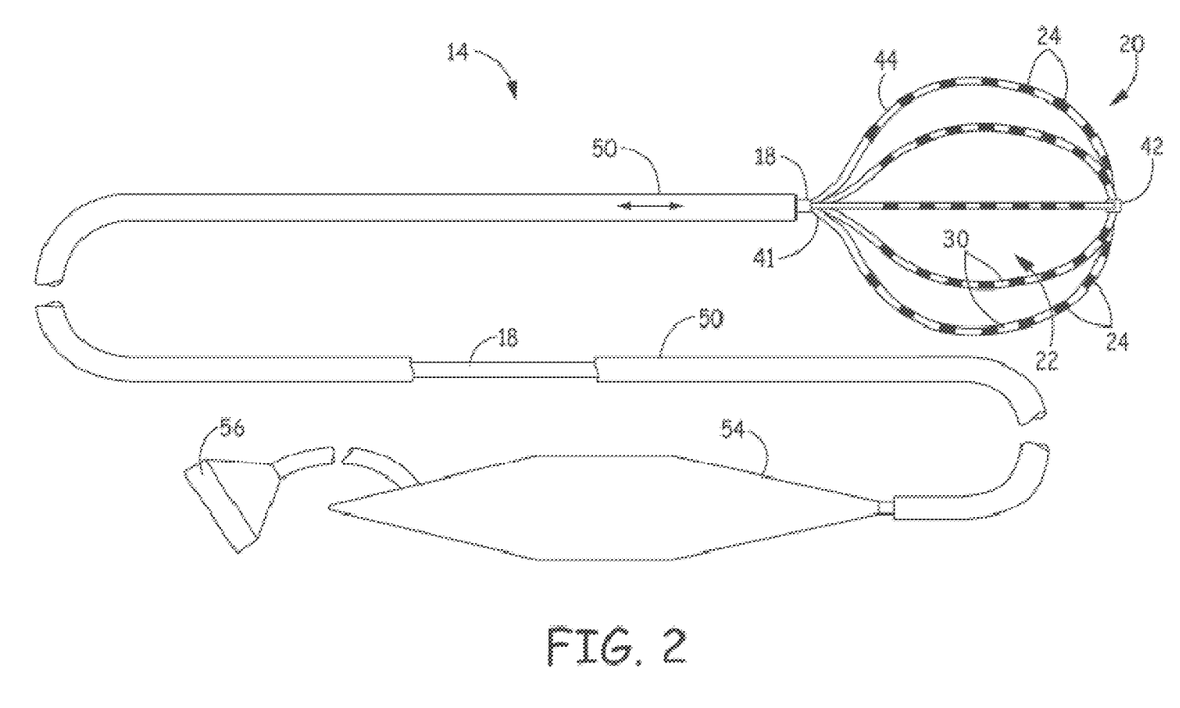
FIG. 2 is a schematic view of an embodiment of a mapping catheter having a basket functional element carrying structure for use in association with the system of FIG. 1.

FIG. 2 illustrates an embodiment of the mapping catheter 14 including electrodes 24 at the distal end suitable for use in the system 10 shown in FIG. 1. The mapping catheter 14 has a flexible catheter body 18, the distal end of which carries the three dimensional structure 20 configured to carry the mapping electrodes or sensors 24. The mapping electrodes 24 sense intrinsic electrical activity, e.g., activation signals, in the myocardial tissue, the sensed activity is then processed by the processing system 32 to assist the physician in identifying the site or sites having a heart rhythm disorder or other myocardial pathology via a generated and displayed APD map. This process is commonly referred to as mapping. This information can then be used to determine an appropriate location for applying appropriate therapy, such as ablation, to the identified sites, and to navigate the one or more ablation electrodes 36 to the identified sites.

The illustrated three-dimensional structure 20 comprises a base member 41 and an end cap 42 between which flexible splines 44 generally extend in a circumferentially spaced relationship. As discussed above, the three dimensional structure 20 takes the form of a basket defining an open interior space 22. In some embodiments, the splines 44 are made of a resilient inert material, such as Nitinol metal or silicone rubber, and are connected between the base member 41 and the end cap 42 in a resilient, pretensed condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is even smaller or larger (e.g., 40 mm in diameter or greater).

A slidable sheath 50 is movable along the major axis of the catheter body 18. Moving the sheath 50 forward (i.e., toward the distal end) causes the sheath 50 to move over the three dimensional structure 20, thereby collapsing the structure 20 into a compact, low profile condition suitable for introduction into and/or removal from an interior space of an anatomical structure, such as, for example, the heart. In contrast, moving the sheath 50 rearward (i.e., toward the proximal end) exposes the three dimensional structure 20, allowing the structure 20 to elastically expand and assume the pretensed position illustrated in FIG. 2. Further details of embodiments of the three dimensional structure 20 are disclosed in U.S. Pat. No. 5,647,870, entitled "Multiple Electrode Support Structures," which is hereby expressly incorporated herein by reference in its entirety.

A signal wire (not shown) is electrically coupled to each mapping electrode 24. The wires extend through the body 18 of the mapping catheter 20 into a handle 54, in which they are coupled to an external connector 56, which may be a multiple pin connector. The connector 56 electrically couples the mapping electrodes 24 to the processing system 32. Further details on mapping systems and methods for processing signals generated by the mapping catheter are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are hereby expressly incorporated herein by reference.

It is noted that other multi-electrode structures could be deployed on the distal end of the mapping catheter 14. It is further noted that the multiple mapping electrodes 24 may be disposed on more than one structure rather than, for example, the single mapping catheter 14 illustrated in FIG. 2. For example, if mapping within the left atrium with multiple mapping structures, an arrangement comprising a coronary sinus catheter carrying multiple mapping electrodes and a basket catheter carrying multiple mapping electrodes positioned in the left atrium may be used. As another example, if mapping within the right atrium with multiple mapping structures, an arrangement comprising a decapolar catheter carrying multiple mapping electrodes for positioning in the coronary sinus, and a loop catheter carrying multiple mapping electrodes for positioning around the tricuspid annulus may be used.

Although the mapping electrodes 24 have been described as being carried by dedicated mapping probes, such as the mapping catheter 14, the mapping electrodes may be carried on non-mapping dedicated probes or multifunction probes. For example, an ablation catheter, such as the ablation catheter 16, can be configured to include one or more mapping electrodes 24 disposed on the distal end of the catheter body and coupled to the signal processing system 32 and guidance system (Not shown in the figures). As another example, the ablation electrode at the distal end of the ablation catheter may be coupled to the signal processing system 32 to also operate as a mapping electrode.

Figure 3:
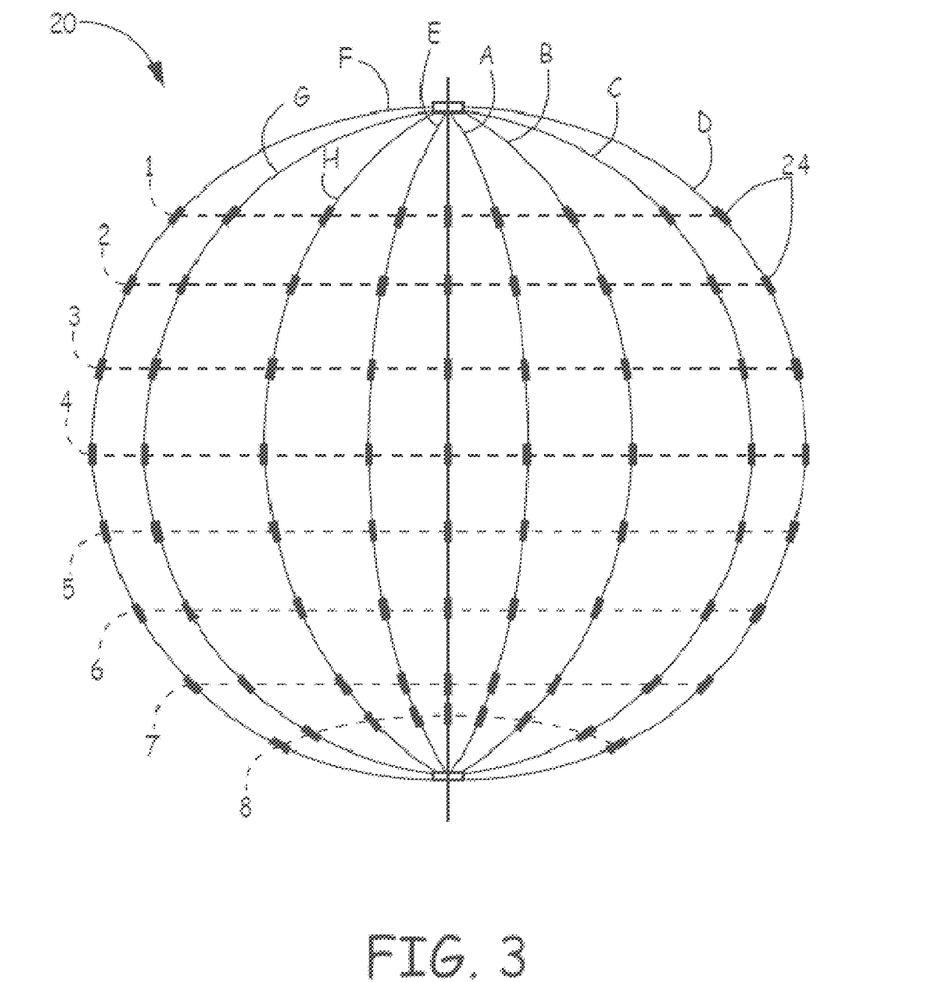
FIG. 3 is a schematic side view of an embodiment of the basket functional element including a plurality of mapping electrodes.

To illustrate the operation of the system 10, FIG. 3 is a schematic side view of an embodiment of the basket structure 20 including a plurality of mapping electrodes 24. In the illustrated embodiment, the basket structure includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on a basket structure 20, the mapping electrodes 24 may alternatively be arranged in different numbers, on different structures, and/or in different positions. In addition, multiple basket structures can be deployed in the same or different anatomical structures to simultaneously obtain signals from different anatomical structures.

After the basket structure 20 is positioned adjacent to the anatomical structure to be treated (e.g., left atrium or left ventricle of the heart), the processing system 32 is configured to record the activation signals from each electrode 24 channel related to intrinsic physiological activity of the anatomical structure, i.e. the electrodes 24 measure electrical activation signals intrinsic to the physiology of the anatomical structure.

The processing system 32 is further configured to generate a persistent display for output to the display device 40. The persistent display includes relevant characteristics pertaining to the sensed activation signals in such a manner that the relevant characteristics corresponding to an intrinsic event remains displayed or persists until the next intrinsic event. The persistent display is updated when a subsequent intrinsic event is detected; therefore, relevant characteristics of the activation signals are not displayed during quiescent periods between the intrinsic events. The intrinsic events may include a cardiac contraction or beat, myocardial electrical activity, electrical signals within neurological pathways, a muscular contraction, or the like.

Figure 4:
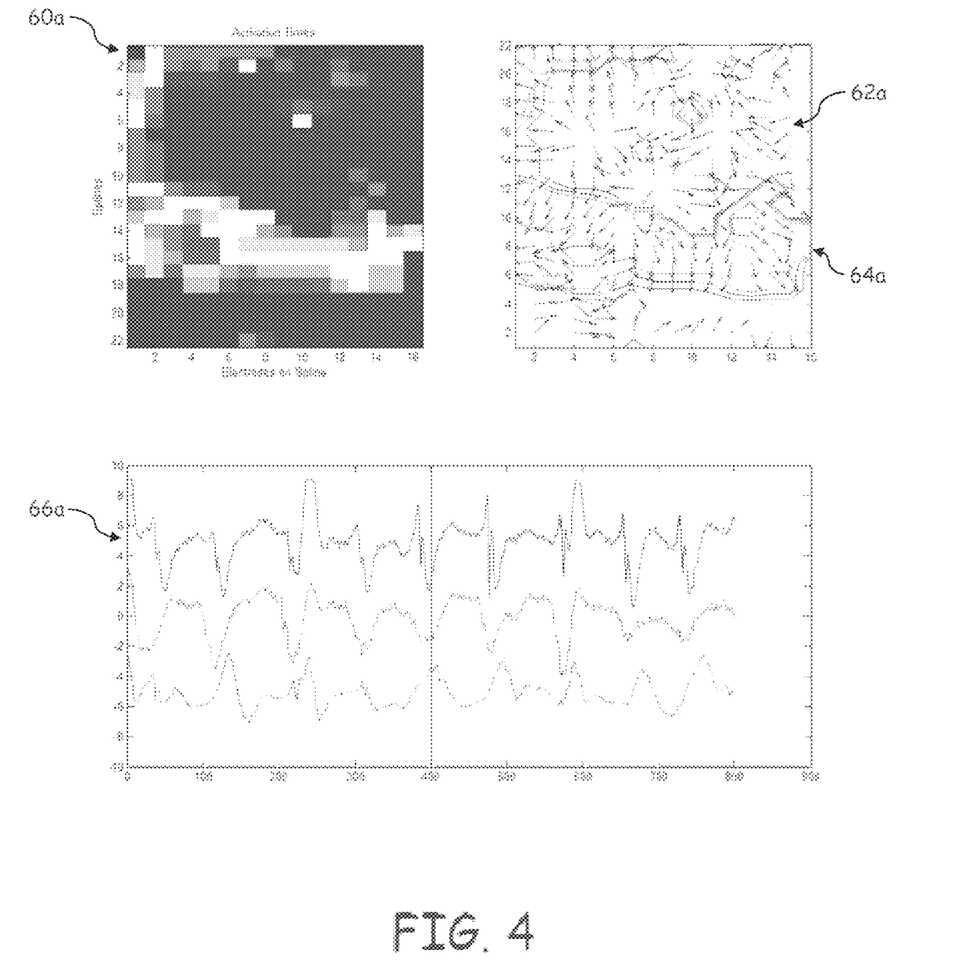
FIG. 4 illustrates a persistent display of relevant characteristics of activation signals sensed by the system of FIG. 1 at a first time.
Figure 5:
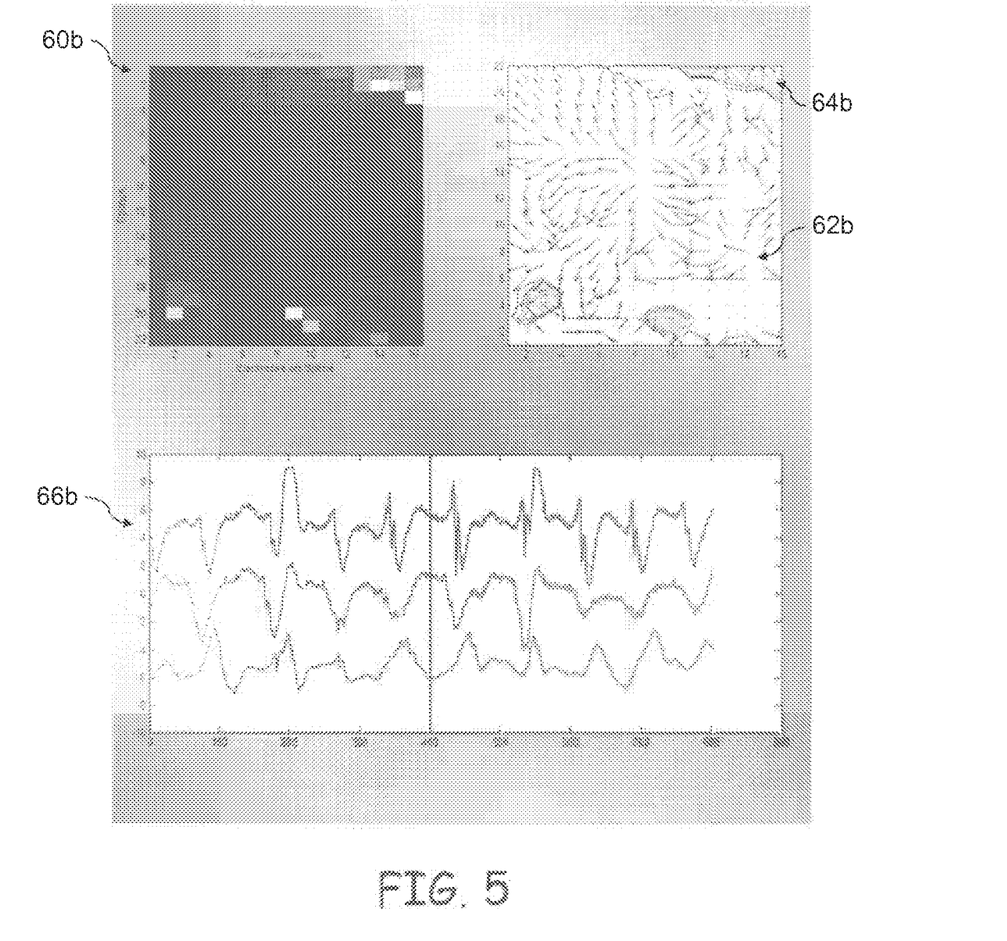
FIG. 5 illustrates the persistent display of FIG. 4 at a subsequent time.

FIGS. 4 and 5 illustrate an example of a persistent display at a time t and a later time t+n, respectively, at which a subsequent intrinsic event has been detected. During a real-time procedure, the display of FIG. 4 will remain persistent until a time period of n passes at which the subsequent intrinsic event occurs and is detected. The processing system 32 detects the intrinsic event and updates the persistent display as shown in FIG. 5. Relevant characteristics may include any one of an activation map 60a & 60b, a vector field showing propagation patterns 62a & 62b, a voltage propagation map such as a contour map of iso-potential lines 64a & 64b which is shown overlaid the vector field but can be also be a separate display, a phase propagation map such as a contour map of iso-phase lines which illustrates the phase propagating across the field of electrodes 24, a derivative map which illustrates the change in voltage over time across the field of electrodes 24, a two-dimensional reliability map (not shown) which indicates a reliability of an onset activation signal for each electrode channel during an intrinsic event under progress, an electrogram 66a & 66b indicating the sensed activation signals at each electrode channel, and the like.

It should be noted that the persistent display can function in a playback mode rather than a real-time mode such that the relevant characteristics remain persistently display until a subsequent intrinsic event is detected whether before a selected time t, as in a playback mode in a reverse direction, or after the selected t, as in a playback mode in a forward direction or in real-time. The user interface of the persistent display, as shown in FIGS. 4 & 5, can also be configurable with various selectable options to choose, for example, how many or which of the various relevant characteristics to be displayed or to view a previous intrinsic event or a future intrinsic event (during a playback mode). Additionally, multiples of a relevant characteristic can be displayed, such as three vectors fields or contour maps where one is designated to display a previous intrinsic event, another is designated to display the most recent intrinsic event, and the final is designated to display a future intrinsic event (during a playback mode). Other options may include highlighting similar intrinsic events based on morphology or a similarity metric based on cross-correlation between the characteristic pattern representing each activity in the vector field map or iso-potential contour map, a similarity metric based on rates of change or patterns in propagation velocity between a given channel, and the like, in the relevant characteristics, e.g. the electrogram. Another option for the persistent display is to modify the vectors of the vector field such that various line weights or colors can denote relationships with previous intrinsic events. A vector to vector cross correlation can be employed by the processing system 32 to generate the changes in line weights or colors.

The processing system 32 determines the most recent intrinsic event before or after a selected time t. The intrinsic event will be described in terms of a cardiac contraction or heart beat (atrial or ventricular hear beat) but can include any measurable electrical signals in a patient's body including, but not limited to, muscle contractions, neurological signals, and the like. The processing system 32 can employ a number of methods to determine the most recent heart beat. In some embodiments, the processing system 32 can determine the most recent heart beat according to a median onset time for the sensed activation signals. An onset time refers to a time stamp associated with each activation signal indicating the initiation of the activation signal. When a heart beat occurs, the myocardial cells in a chamber of interest do not depolarize at the same time. Therefore, the mapping electrodes 24 will sense activation signals at various times within a small window depending on their location with respect to, for example, an electrical impulse node. By taking the median onset times of these activation signals, the processing system 32 can approximate a time stamp for the corresponding heart beat. If the time stamp is the same as the previous heart beat, then a subsequent heart beat has not been detected and the processing system does not update the persistent display, i.e. the information and/or data that is displayed persists until a subsequent heart beat is detected. Once the processing system 32 detects a median onset time which differs from a median onset time of a previously detected heart beat, the processing system 32 updates the persistent display with relevant characteristics derived from the activation signals associated with the current or most recently detected heart beat.

In some embodiments, the processing system 32 is configured to determine the most recent beat calculate the sum of squares of the activation signals across a plurality of mapping electrode 24 channels wherein the resultant composite signal peaks are indicative of beat timings. Alternatively, the processing system 32 can determines the most recent heart beat according to a convolution of a train of onset times for each electrode with a smoothing function such as a Gaussian function. The convoluted functions can be summed across a plurality of mapping electrode 24 channels wherein the peaks on the summed or composite signal can indicate beat timings.

In some embodiments, the processing system 32 determines the most recent heart beat according to a morphology comparison between the activation signals or relevant characteristics of a previous heart beat and the most recent heart beat. If a significant change in the morphology is detected by the processing system 32, the relevant characteristics of the persistent display will be updated based on the activation signals corresponding to the most recent heart beat.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An anatomical mapping system comprising:
a mapping probe, the mapping probe comprising a catheter body and a three-dimensional multiple electrode structure disposed at a distal end of the catheter body, the three-dimensional multiple electrode structure comprising a plurality of mapping electrodes configured to be positioned within an anatomical structure and to detect activation signals of intrinsic events within the anatomical structure, each of the plurality of mapping electrodes having an electrode location; and
a processing system associated with the plurality of mapping electrodes, the processing system configured to record the detected activation signals and associate at least one of the plurality of mapping electrodes with each recorded activation signal, the processing system further configured to:
determine a first intrinsic event associated with a first time;
generate a persistent display of at least one relevant characteristic of the detected activation signals of the first intrinsic event;
determine a second intrinsic event associated with a second time;
update, in a real-time mode, the persistent display with at least one relevant characteristic of the second intrinsic event upon the determination of the second intrinsic event;
display, simultaneously, in a playback mode, a representation of the first intrinsic event and a representation of the second intrinsic event;
determine a similarity metric associated with the first and second intrinsic events, wherein the similarity metric is based on a cross-correlation between a first characteristic pattern and a second characteristic pattern, the first and second characteristic patterns representing the first event and the second intrinsic events, respectively, in at least one of a vector field map and an iso-potential contour map; and
highlight, on a user interface of the persistent display, in the playback mode, and based on the similarity metric, the representations of the first and second intrinsic events to indicate that the first and second intrinsic events are similar intrinsic events.

2. The anatomical system according to claim 1, wherein the persistent display includes at least one of an activation map, a vector field representing an activation pattern, a voltage propagation map representing voltage propagation pattern, a phase propagation map representing phase propagation pattern, a derivative map representing a pattern in a change of voltage over time, and a reliability map representing a reliability pattern related to onset pick-up times of the activation signals.

3. The anatomical system according to claim 1, wherein, to determine the second intrinsic event, the processing system is further configured to determine an onset time for the most recent activation signal at each of the plurality of electrodes, and to calculate a median onset time based on an average of the determined onset times.

4. The anatomical system according to claim 1, wherein, to determine the second intrinsic event, the processing system is further configured to calculate a quadratic mean for the most recent activation signal for each of the plurality of electrodes, and to determine a peak value from a sum of the quadratic means across the plurality of mapping electrodes.

5. The anatomical system according to claim 1, wherein, to determine the second intrinsic event, the processing system is further configured to determine an onset time for the most recent activation signal at each of the plurality of electrodes, convolve the onset times with a smoothing function, and determine a peak value from a sum of the convolved signals across the plurality of electrodes.

6. The anatomical system according to claim 1, the processing system being further configured to: determine a morphology for each intrinsic event, compare the morphology of the second intrinsic event with the first intrinsic event, and update the persistent display based on changes in morphology between the second and first intrinsic event.

7. The anatomical system according to claim 1, wherein the second intrinsic event is an intrinsic event that is detected nearest to the first intrinsic event.

8. The anatomical system according to claim 1, wherein the persistent display is generated in real-time as the activation signals are detected.

9. The anatomical system according to claim 1, wherein the persistent display is generated off line after a plurality of activation signals are recorded and the second intrinsic event is before or after the first time.

10. The anatomical system according to claim 1, wherein the first intrinsic event and the second intrinsic event include at least one of the following: a cardiac contraction, a cardiac beat, a myocardial electrical activity, an electrical signal within a neurological pathway, and a muscular contraction.

11. An anatomical mapping system comprising:
- a mapping probe, the mapping probe comprising a catheter body and a three-dimensional multiple electrode structure disposed at a distal end of the catheter body, the three-dimensional multiple electrode structure comprising a plurality of mapping electrodes configured to be positioned within an anatomical structure and to detect activation signals of intrinsic events within the anatomical structure, each of the plurality of mapping electrodes having an electrode location; and
- a processing system associated with the plurality of mapping electrodes, the processing system configured to record the detected activation signals and associate at least one of the plurality of mapping electrodes with each recorded activation signal, the processing system further configured to:
  - determine a first intrinsic event associated with a first time;
  - generate a persistent display of at least one relevant characteristic of the detected activation signals of the first intrinsic event, the persistent display comprising a vector field map representing an activation pattern;
  - determine a second intrinsic event associated with a second time;
  - update the persistent display with at least one relevant characteristic of the second intrinsic event upon the determination of the second intrinsic event;
  - determine a similarity metric based on a cross-correlation between a first characteristic pattern and a second characteristic pattern, the first and second characteristic patterns representing the first intrinsic event and the second intrinsic event, respectively, in the vector field map; and
  - highlight, on a user interface of the persistent display and based on the similarity metric, representations of the first and second intrinsic events to indicate that the first and second intrinsic events are similar intrinsic events.

* * * * *